(12) United States Patent
Talalay et al.

(10) Patent No.: US 8,927,007 B2
(45) Date of Patent: Jan. 6, 2015

(54) FORMULATIONS FOR TREATMENT WITH GLUCOSINOLATES

(76) Inventors: Paul Talalay, Baltimore, MD (US); Jed Fahey, Reistertown, MD (US); Antony Talalay, Lutherville, MD (US)

( * ) Notice: Subject to any disclaimer, the term of this patent is extended or adjusted under 35 U.S.C. 154(b) by 0 days.

(21) Appl. No.: 13/577,181

(22) PCT Filed: Sep. 14, 2011

(86) PCT No.: PCT/US2011/051511
§ 371 (c)(1),
(2), (4) Date: Dec. 19, 2012

(87) PCT Pub. No.: WO2012/037193
PCT Pub. Date: Mar. 22, 2012

(65) Prior Publication Data
US 2013/0164365 A1     Jun. 27, 2013

Related U.S. Application Data

(60) Provisional application No. 61/383,853, filed on Sep. 17, 2010.

(51) Int. Cl.
| | | |
|---|---|---|
| A61K 38/47 | (2006.01) | |
| A61K 31/7028 | (2006.01) | |
| A61K 31/26 | (2006.01) | |
| A23L 1/305 | (2006.01) | |
| A23L 1/03 | (2006.01) | |
| A61K 9/00 | (2006.01) | |
| A61K 9/06 | (2006.01) | |
| A61K 9/127 | (2006.01) | |

(52) U.S. Cl.
CPC ............. *A61K 38/47* (2013.01); *A61K 31/7028* (2013.01); *A61K 31/26* (2013.01); *A23L 1/305* (2013.01); *A23L 1/034* (2013.01); *A61K 9/0014* (2013.01); *A61K 9/06* (2013.01); *A61K 9/127* (2013.01); *C12Y 302/01147* (2013.01)
USPC .......................... 424/450; 424/94.61; 424/400

(58) Field of Classification Search
None
See application file for complete search history.

(56) References Cited

U.S. PATENT DOCUMENTS

| | | |
|---|---|---|
| 5,227,459 A | 7/1993 | Pawelek et al. |
| 2005/0063965 A1 | 3/2005 | Gao et al. |
| 2008/0311192 A1 * | 12/2008 | West et al. ...................... 424/463 |
| 2008/0312164 A1 | 12/2008 | Rajski |
| 2009/0081138 A1 | 3/2009 | Ashurst |
| 2009/0247477 A1 * | 10/2009 | Talalay et al. .................... 514/24 |
| 2010/0172941 A1 * | 7/2010 | Vajdy et al. ................. 424/283.1 |
| 2010/0183740 A1 * | 7/2010 | Feng ............................. 424/641 |
| 2010/0317518 A1 | 12/2010 | Stevens et al. |
| 2011/0014137 A1 | 1/2011 | Talalay et al. |

OTHER PUBLICATIONS

The Search Report received in the corresponding patent application No. PCT/US2011/051511, dated Jun. 1, 2012.

* cited by examiner

*Primary Examiner* — Brian Gulledge
*Assistant Examiner* — Celeste A Roney
(74) *Attorney, Agent, or Firm* — Cermak Nakajima & McGowan LLP; Malcolm K. McGowan

(57) ABSTRACT

The application relates to topical formulations comprising a phase II enzyme inducer precursor and an activating agent. Methods for producing and using the topical formulations are also provided.

33 Claims, No Drawings

FORMULATIONS FOR TREATMENT WITH GLUCOSINOLATES

This application claims priority from U.S. Provisional Application 61/383,853, filed Sep. 17, 2010, incorporated herein by reference in its entirety

BACKGROUND

Skin ailments affect millions of people worldwide and cost billions of dollars in treatment costs. While the causes of skin ailments can come from many sources, exposure to ultraviolet (UV) and solar radiation is a common cause to many skin ailments.

Continued exposure to UV and solar radiation can directly damage DNA, generate reactive oxidants that peroxidize lipids, and damage other cellular components. UV and solar radiation can also initiate inflammation and suppress the immune response. The effects of such damage include changing the elasticity and content of skin, accelerating the aging of skin (dermatobeliosis), and causing raised, reddish, rough-textured growths (keratoses). U.S. Pat. No. 6,079,415. In some cases, too much sun exposure causes skin cells to develop into tumorous growths, which can then become skin cancer. Additional skin ailments include erythema, epidermolysis bullosa simplex, and the effects of aging, such as wrinkles, sagging skin, dry skin, age spots, and fine lines.

It is now widely accepted that UV radiation is the main factor responsible for the majority of nonmelanoma skin cancers. UV radiation is probably the most ubiquitous environmental carcinogen and the principal factor contributing to nonmelanoma skin cancers. At least three different effects of exposure to UV radiation contribute to the process of carcinogenesis in the skin: (i) direct DNA damage leading to the formation of DNA photoproducts, e.g., clycobutane-pyrimidine dimers and pyrimidine-pyridmidine products, (ii) oxidative stress-related DNA damage resulting from the formation of reactive oxygen intermediates, and (iii) immunosuppression that raises tolerance to genetic instability. See Setlow et al. *J. Mol. Biol.* (1966) vol. 17, pp. 237-54; Sander et al. *Int. J. Dermatol.* (2004) vol. 43, pp. 326-35; and Nishigori et al. *J. Investig. Dermatol. Symp. Proc.* (1996) vol. 1, pp. 143-46.

Skin cancer incidence is steadily rising and has reached epidemic proportions. The average rise in new skin cancer diagnoses has been 3-8% per year since the 1960's and non-melanoma skin cancers are now the most common types of cancer in the United States, with over 1 million new cases per year. Alam et al. *N. Engl. J. Med.* (2001) vol. 344, pp. 975-83. See also WO 2006/118941.

Many types of chemoprotectors against cancer evoke large inductions of phase II enzymes of xenobiotic metabolism and increase glutathione levels in animal tissues. See Talalay et al. *Toxicol. Lett.* (1995) vol. 82/83, pp. 173-79. These cellular responses accelerate the detoxication of electrophiles and reactive forms of oxygen, and thereby protect cells against mutagenesis and neoplasia. Substantial evidence suggests that induction of these detoxication enzymes provides a major strategy for achieving protection against malignancy. See Talalay et al., supra. Phase II enzymes include Quinone reductase (NAD(P)H:oxidoreductase), Gluthathione S-transferases, and Glucuronosyltransferases. Additional phase II enzymes are described in U.S. Patent Application Publication No. 2005/0063965, hereby incorporated by reference in its entirety for all purposes. See e.g., pg. 4, para. [0046].

One strategy of fighting cancer is to invoke the activity of phase II enzymes through their inducers. Inducers include monofunctional inducers such as diphenol, thiocarbamate, 1,2-dithiol-3-thiones, and isothiocyanates. Sulforaphane (4-methylsulfinylbutyl isothiocyanate) and its analogs, described by U.S. Patent Application Publication No. 2005/0063965, incorporated here by reference in its entirety for all purposes, are illustrative examples of phase II enzyme inducers.

Isothiocyanates are found in various plants, including those from the Brassicae family and comprising broccoli, cauliflower, kale, brussel sprouts, arugula, cabbage, Chinese cabbage, collards, crambe, daikon, kohlrabi, mustard, red radish, turnip, and watercress. Isothiocyanates are generally produced when their precursors, glucosinolates, (β-thioglucoside N-hydrosulfate), are hydrolyzed by the enzyme myrosinase (β-thioglucoside glucohydrolase). In the plants described, glucosinolate and myrosinase are kept separate. This is possibly to prevent premature hydrolysis of glucosinolates into isothiocyanates.

Formulations comprising glucosinolates and myrosinase in separated form is desired to treat and prevent skin ailments as well as other cancerous conditions.

SUMMARY

Topical formulations comprising a phase II enzyme inducer precursor and an activating agent are provided. Contact between the precursor and activating agent is substantially reduced such that there is little or no contact between the two compounds. Methodology for producing and using the topical formulations are also provided.

One benefit of substantially separating the precursor and agent is to reduce the likelihood of premature activation. The topical formulation provided herein can therefore be stored for a relatively long period of time and maintain the potency of the precursor such that the formulation can have a therapeutic effect when used.

In one embodiment, a topical formulation is provided comprising: (a) at least one phase II enzyme inducer precursor and (b) at least one activating agent, wherein contact between said precursor and agent is substantially reduced during storage.

In another embodiment, the precursor is a glucosinolate. In a specific embodiment, the glucosinolate is glucoraphanin.

In another embodiment, the agent is a myrosinase.

In another embodiment, the inducer is an isothiocyanate. In a specific embodiment, the isothiocyanate is sulforaphane.

In another embodiment, the precursor and the agent are each encapsulated.

In another embodiment, the precursor and the agent are encapsulated in a carrier selected from the group comprising a micelle, a liposome, and a microsphere.

In another embodiment, the precursor and the agent are encapsulated separately.

In another embodiment, the precursor and the agent are separated by a thin layer.

In another embodiment, the precursor and the agent are not encapsulated.

In another embodiment, the precursor and the agent are placed in separate chambers in a container.

In another embodiment, the precursor and the agent are placed in a thixotropic medium.

In another embodiment, the formulation is selected from the group comprising a cream, a lotion, a gel, an ointment, a paste, and an aerosol spray.

In another embodiment, the formulation is sterile at least prior to a first use of the formulation.

In another embodiment, the formulation further comprises an antimicrobial composition.

In another embodiment, the antimicrobial composition is benzyl alcohol.

In another embodiment, a method of making a topical formulation is provided, comprising: (a) providing at least one phase II enzyme inducer precursor; (b) providing at least one activating agent; (c) providing a medium; and (d) forming the topical formulation by including elements (a), (b), and (c) therein.

In another embodiment, the precursor is a glucosinolate. In a specific embodiment, the glucosinolate is glucoraphanin.

In another embodiment, the activating agent is a myrosinase.

In another embodiment, the medium is selected from the group comprising of a cream, a lotion, a gel, an ointment, a paste, and an aerosol.

In another embodiment, the precursor and the activating agent are encapsulated.

In another embodiment, either the precursor or the activating agent is encapsulated.

In another embodiment, the encapsulation is in a carrier selected from the group comprising a micelle, a liposome, and a microsphere.

In another embodiment, the method further provides an antimicrobial composition.

In another embodiment, step (d) comprises placing the precursor and the activating agent in separate containers.

In another embodiment, the medium is a thixotropic material.

In another embodiment, a method of treating skin ailments is provided, comprising: (a) providing a topical formulation; (b) applying the formulation to the surface of skin; and (c) applying pressure or shear stress to the formulation onto the skin.

In another embodiment, the topical formulation comprises at least one phase II enzyme inducer precursor and at least one activating agent such that contact between the precursor and the agent is substantially reduced.

In another embodiment, the precursor and the agent are each encapsulated in a carrier selected from the group comprising a micelle, a liposome, and a microsphere.

In another embodiment, the topical formulation is provided in a medium selected from the group comprising a cream, a lotion, a gel, an ointment, a paste, and an aerosol spray.

In another embodiment, step (b) comprises providing pressure or stress onto said medium such that the carrier is not broken or does not release the precursor or activating agent.

In another embodiment, a method of treating skin ailments is provided, comprising: (a) providing a topical formulation in a container, wherein the topical formulation comprises at least one phase II enzyme inducer precursor and at least one activating agent, wherein contact between the precursor and agent is substantially reduced; (b) mixing the precursor and agent together to create a mixture; and (c) applying the mixture to the surface of skin.

In another embodiment, the container is selected from the group comprising a syringe, a tube, and a dispensing apparatus.

In another embodiment, the topical formulation further comprises a medium selected from the group comprising a cream, a lotion, a gel, an ointment, and a paste.

In another embodiment, the precursor and the agent are encapsulated in a carrier selected from the group comprising a micelle, a liposome, and a microsphere.

In another embodiment, step (b) comprises providing pressure or stress onto said medium such that said carrier is not broken or does not release said precursor or activating agent.

In another embodiment, a method of treating skin cancer is provided, comprising: (a) providing a topical formulation comprising at least one phase II enzyme inducer precursor and at least one activating agent, wherein the precursor and agent are each encapsulated in a carrier such that contact between said precursor and said agent is substantially reduced; (b) mixing the carriers containing said precursor and said agent together to create a mixture; and (c) applying the mixture to the surface of skin.

In another embodiment, the precursor is a glucosinolate. In a specific embodiment, the glucosinolate is glucoraphanin.

In another embodiment, the agent is a myrosinase.

In another embodiment, the phase II enzyme is an isothiocyanate. In a specific embodiment, the isothiocyanate is sulforaphane.

In another embodiment, the topical formulation further comprises a dermal penetration-enhancing compound.

In another embodiment, the method of treating comprises applying the mixture to the surface of skin after skin damage.

In another embodiment, the method of preventing comprises applying the mixture to the surface of skin before skin damage.

DETAILED DESCRIPTION

Provided herein are topical formulations and methodology for making and using the topical formulations. The topical formulations are applied to the surface of skin such that an active ingredient within the formulations can penetrate the skin. Active ingredients provided herein include phase II enzyme inducer precursors and their activating agents.

The topical formulation can include various types of mediums in which the precursors and activating agents are provided. These mediums are disclosed herein and include, but are not limited to, creams, lotions, gels, ointments, pastes, and aerosols.

Various ways of providing for separation between the precursors and their activating agents are described herein, including but not limited to, by encapsulation (such as via micelles, liposomes, or microspheres), by device, and by the topical formulation medium.

Various ways of making the precursors and their activating agents come together after being separated are also described herein, including but not limited to, by force (such as pressure or shear stress) and by environment change (such as changes in pH, moisture, and temperature).

The topical formulation can be applied to the skin directly from a container by the method of, including but not limited to, rubbing, spraying, and combinations thereof. The formulation can also be applied with a dropper, swab, or other devices.

The activity of the phase II enzyme inducer precursors and their activating agents can repair skin ailments after they have occurred. In addition phase II enzyme inducer precursors and their activating agents can prevent damage that has already been initiated. "Repair" encompasses treating or curing damage that has already occurred. "Preventing" encompasses the situation where a person has no skin ailment and the topical formulation could be applied as a preventative measure in stopping damage from occurring in the first place.

"Phase II enzyme" hereby includes enzymes that have health-promoting activities, including antioxidant activity. Such enzymes include, for example, Quinone reductase (NAD(P)H:oxidoreductase), Gluthathione S-transferases, Glucuronosyltransferases, and other enzymes described in U.S. Patent Application Publication No. 2005/0063965 incorporated by reference above.

"Phase II enzyme inducer" hereby includes compounds that activate phase II enzymes, such as, but not limited to, diphenols, thiocarbamate, 1,2-dithiol-3-thiones, and isothiocyanates including sulforaphane (4-methylsulfinylbutyl isothiocyanate) and its analogs described in U.S. Patent Application Publication No. 2005/0063965, incorporated by reference above. Isothiocyanates are not water soluble, but are highly fat soluble (lipophilic).

"Phase II enzyme inducer precursor" hereby includes, but is not limited to, glucosinolate, as described in U.S. Patent Application Publication No. 2006/0127996, incorporated by reference in its entirety for all purposes.

"Activating agent" hereby includes, but is not limited to, myrosinase (β-thioglucoside glucohydrolase).

"Substantially reduced" hereby includes separation of components in the topical formulation such that contact is minimized.

"During storage" hereby includes keeping the topical formulation within a container for any period of time.

Skin Ailments

Skin ailments include but are not limited to dermatobeliosis (accelerated aging of skin), keratoses (raised, reddish, rough-textured growths), altered elasticity and content of skin, skin cancer, erythema, epidermolysis bullosa simplex, and the effects of aging.

Skin cancer includes non-melanoma skin cancer such as basal cell carcinoma and squamous cell carcinoma, and melanoma skin cancer.

The effects of aging include wrinkles, sagging skin, dry skin, age spots, and fine lines.

Glucosinolates

Glucosinolates, β-thioglucoside N-hydroxysulfates with a side chain and a sulfur-linked β-D-glucopyranose moiety, are found in a variety of plants, both cruciferous and non-cruciferous. Generally, angiosperm families that contain glucosinolate chemicals include: Bataceae, Brassicaceae, Bretschneideraceae, Capparaceae, Caricaceae, Euphorbiaceae, Gyrostemonaceae, Limnanthaceae, Moringaceae, Pentadiplandraceae, Phytolaccaceae, Pittosporaceae, Resedaceae, Salvadoraceae, Tovariaceae, and Tropaeolaceae. Most of the plants containing glucosinolate fall within the Brassicaceae, Capparaceae, and Caricaeae families. Fahey et al. *Phytochemistry* (2001) 56:5-51.

Glucosinolates are found in abundance in the seeds and sprouts of many species of the above-mentioned families, including Broccoli seeds and sprouts in the Brassiceae family.

Glucosinolates can also be obtained from extracts of any of the above- and below-mentioned species of plants.

Glucosinolates can be categorized in the following classes: aliphatic, ω-methylthioalkyl, aromatic and heterocyclic (i.e. indole).

Specific glucosinolate chemicals include the following: 3-Methyoxycarbonylpropyl, 1-Acetyl-indol-3-ylmethyl, 4-(4'-O-Acetyl-α-L-rhamnopyranosyloxy)benzyl, 2-(α-L-Arabinopryanosyloxy)-2-phenylethyl, 4-(Benzoyloxy)butyl, 2-(Benzoyloxy)ethyl, 2-Benzoyloxy-1-ethylethyl, Benzoyloxymethyl, 2-Benzoloxy-1-methylethyl, 3-(Benzoyloxy) propyl, Benzyl, 3-Butenyl, n-Butyl, 3,4-Dihydroxybenzyl, 3,4-Dimethoxybenzyl, Etyl, 1-Ethyl-2-hydroxyethyl, 6-Heptenyl, 5-Hexenyl, n-Hexyl, 2-Hydroxybenzyl, 3-Hydroxybenzyl, 4-Hydroxybenzyl, 2(R)-2-Hydroxy-3-butenyl, 2(S)-2-Hydroxy-3-butenyl, 3-Hydroxybutyl, 4-Hydroxybutyl, 2-Hydroxyethyl, 4-Hydroxyindol-3-ylmethyl, 2-Hydroxyl-2-methylbutyl, 1-(Hydroxymethyl)propyl, 2-Hydroxy-2-methylpropyl, 3-Hydroxy-6-(methylsufinyl)hexyl, 3-Hydroxy-5-(methylsufinyl)pentyl, 3-Hydroxy-6-(methylsulfonyl) hexyl, 3-Hydroxy-5-(methylsulfonyl)pentyl, 3-Hydroxy-6-(methylthio)hexyl, 3-Hydroxy-5-(methylthio)pentyl, 2-Hydroxyl-4-pentenyl, 2-Hydroxypentyl, 2(R)-Hydroxy-2-phenylethyl, 2-Hydroxypropyl, 3-Hydroxypropyl, Indol-3-ylmethyl, 2-Methoxybenzyl, 3-Methoxybenzyl, 4-Methoxybenzyl, 1-Methoxyindol-3-ylmethyl, 4-Methoxyindol-3-ylmethyl, 2-(4-Methoxyphenyl)-2,2-dimethylethyl, 2-(4-Methoxyphenyl)-2-hydroxyethyl, Methyl, 3-Methyl-3-butenyl, 1-Methylbutyl, 2-Methylbutyl, 3-Methylbutyl, 1-Methylethyl, 1-Methyl-2-hydroxyethyl, 3-Methylpentyl, 4-Methylpentyl, 2-Methyl-2-propenyl, 1-Methylpropyl, 2-Methylpropyl, 4-Methylsulfinyl-3-butenyl, 4-(Methylsulfinyl)butyl, 10-(Methylsulfinyl)decyl, 7-(Methylsulfinyl) heptyl, 6-(Methylsulfinyl)hexyl, 9-(Methylsulfinyl)nonyl, 8-(Methylsulfinyl)octyl, 7-Methylsufinyl-3-oxoheptyl, 8-Methylsulfinyl-3-oxooctyl, 5-(Methylsulfinyl)pentyl, 3-(Methylsulfinyl)propyl, 11-(Methylfulfinyl)undecyl, 4-Methylsulfynol-3-butenyl, 4-(Methylsulfonyl)butyl, 10-(Methylsulfonyl)decyl, 6-(Methylsulfonyl)hexyl, 9-(Methylfsulfonyl)nonyl, 8-(Methylsulfonyl)octyl, 5-(Methylsulfonyl)pentyl, 3-(Methylsulfonyl)propyl, 4-Methylthio-3-butenyl, 4-(Metylthio)butyl, 10-(Methylthio)decyl, 2-(Methylthio)ethyl, 7-(Methylyhio)heptl, 6-(Methylthio) hexyl, 9-(Methylthio)nonyl, 7-Methylthio-3-oxoheptyl, 6-Methylthio-3-oxohexyl, 8-(Methylthio)octyl, 8-Methylthio-3-oxooctyl, 5-(Methylthio)pentyl, 3-(Methylthio)propyl, 4-Oxoheptyl, 5-Oxoheptyl, 5-Oxooctyl, 4-Oxopentyl, 1-Pentenyl, 4-Pentenyl, n-Pentyl, Phenyl, 4-Phenylbutyl, 2-Phenylethyl, 3-Phenylpropyl, 2-Propenyl, n-Propyl, 2-(α-L-Rhamnopyranosyloxy)benzyl, 4-(α-L-Rhamnopyranosyloxy)benzyl, 6-Sinapoyl-β-D-1-thioglucoside of 4-methylsulfinylbut-3-enyl, 1-Sulfo-indol-3-ylmethyl, 4,5,6,7-Tetrahydroxydecyl, 3,4,5-Trimethixybenzyl, "iso"-Heptyl, "iso"-Hexyl, 5-(Benzoyloxy)pentyl, 6-(Benzoyloxy)hexyl, 2-O-Apiosylglucomatronalin, and 3-O-Apiosylglucomatronalin 3,4-dimethoxybenzoyl ester.

Topical Formulation Medium

The topical formulation can be provided in a variety of mediums, including but not limited to, creams, emulsions, lotions, gels, and aerosols as described in U.S. Pat. Nos. 4,844,902; 6,818,226; 6,469,015; 7,147,854; 7,192,607; 7,205,003; and 7,252,831, hereby incorporated by reference in their entirety for all purposes. The medium can be water- or oil-based.

Creams

Creams provided herein include liquids or semi-solid emulsions with a viscous consistency. Creams can be either oil-in-water or water-in-oil based formulations. Cream bases can be water soluble. Cream bases can contain the following components: (1) an oil phase, (2) an aqueous phase, and (3) an emulsifier. The oil phase can comprise petroleum jelly and a fatty alcohol, such as cetyl or stearyl alcohol. The aqueous phase can contain a humectant. The emulsifier can be a non-ionic, anionic, cationic or amphoteric surfactant.

In one embodiment, the oil phase includes, but is not limited to, cetyl alcohol, stearyl alcohol, stearic acid, liquid paraffin, and dimethicone In another embodiment, the water phase ingredient includes, but is not limited to, glycerol and ethyl paraben.

In another embodiment, the emulsifying agent includes, but is not limited to, fatty alcohol polyoxyethylene ether (Peregal A-20), polyoxylstearate (SG-6), or combinations thereof.

Lotions

Lotions provided herein include liquids or semi-liquid formulations comprising solid particles suspended in a water or alcohol base. The lotions can be an oil-in-water formulation stabilized by a surface-active agent.

In one embodiment, the solid particles are finely divided.

In another embodiment, the lotions contain suspending agents to produce better dispersions and compounds useful for localizing and holding the active agent in contact with the skin, including methylcellulose, sodium carboxymethyl-cellulose, and similar compounds.

In another embodiment, because lotions may separate or stratify, they should be well shaken before each use.

Gels

Gels provided herein include semi-solid suspension systems. The gels can be single- or two-phase systems. The gels can be oil or liquid based. Single-phase gels can contain small organic macromolecules distributed substantially uniformly throughout a liquid, such that the there is no boundary between the macromolecules and liquid. The liquid can be aqueous, but also contain an alcohol, and, optionally, an oil. Single-phase gels can be made from synthetic macromolecules or from natural gums. Two-phase gels can include a network of small, discrete particles. In one embodiment, two-phase gels are thixotropic.

In one embodiment, the organic macromolecules include crosslinked acrylic acid polymers such as the "carbomer" family of polymers (i.e., carboxypolyalkylenes). The organic macromolecules can also be hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin.

In another embodiment, the organic macromolecules having a stabilizing action include long-chain linear high molecular weight polysaccharides with a molecular weight of more than one million. In this embodiment, 0.1 to 1.5% of such stabilizers are included.

In another embodiment, a uniform gel can be prepared by adding dispersing agents such as alcohol or glycerin.

In another embodiment, the organic macromolecules can be dispersed by trituration, mechanical mixing or stirring, or combinations thereof.

In another embodiment, the liquid can be either water or all water-miscible solvents. Examples of applicable solvents include alkanols, such as ethanol and isopropyl alcohol, benzyl alcohol, propylene glycol and similar solvents.

Ointments

Ointments provided herein include semi-solid preparations that have petroleum jelly or their derivatives as a base. Petroleum jelly is a semi-solid mixture of hydrocarbons. As described in Remington: The Science and Practice of Pharmacy, 19th Ed. (Easton, Pa.: Mack Publishing Co., 1995), at pages 1399 1404, ointment bases can be grouped in four classes: oleaginous bases; emulsifiable bases; emulsion bases; and water-soluble bases. Oleaginous ointment bases include vegetable oils, fats obtained from animals, and semi-solid hydrocarbons obtained from petroleum. Emulsifiable ointment bases, also known as absorbent ointment bases, contain little or no water and include, for example, hydroxystearin sulfate, anhydrous lanolin, and hydrophilic petroleum jelly. Emulsion ointment bases are either water-in-oil or oil-in-water emulsions, and include, for example, cetyl alcohol, glyceryl monostearate, lanolin, and stearic acid.

Pastes

Pastes included herein contain, in addition to an ointment or cream base, high amounts of pulverulent constituents, such as zinc oxide, talc, starch or titanium dioxide.

In one embodiment, the paste is selected from the group comprising fatty pastes or single-phase aqueous gels. The fatty paste includes petroleum jelly, hydrophilic petroleum jelly, or other similar compounds. The single-phase aqueous gel can incorporate carboxymethylcellulose or similar compounds.

Aerosols

Aerosol provided herein include products packaged under pressure and contain ingredients that are released upon activation of an appropriate valve system. Aerosols include all self-contained pressurized products, such as fine mists of spray or foam, that are emitted from a pressurized container containing a propellant, foams, or semisolid liquids.

In one embodiment, the aerosol comprises a container, a propellant, a concentrate containing an active ingredient, a valve (which may be a metered valve), and an actuator. The nature of these components determines characteristics such as delivery rate, foam density, and fluid viscosity.

In another embodiment, the aerosol is a two-phase formulation comprising a gas and liquid.

In another embodiment, the aerosol is a three-phase formulation comprising a gas, liquid, and suspension or emulsion of active ingredients. In this formulation, suitable excipients, such as wetting agents and/or solid carriers such as talc or colloidal silicas are included.

In another embodiment, the propellant is liquefied or vaporized.

In another embodiment, a solvent can be the propellant or a mixture of the propellant and co-solvents such as alcohol and polyethylene glycols.

In another embodiment, the propellant is selected from the group comprising a spray, foam, or quick-breaking foam.

In another embodiment, spray formulations are aqueous solutions in a container having a spray means, such as an atomizer or nebulizer.

Other Elements in Topical Formulation

The topical formulations provided herein can include additional elements to affect the physical or functional characteristics of the formulations.

Stabilizers, preservatives, humectants, regreasing agents, solvents or auxiliaries can be included to improve efficacy and dermal penetration.

Dermal penetration-enhancing compounds provided have low toxicity to the skin and can promote percutaneous and oral mucosal absorption. In one embodiment, dermal penetration-enhancing compounds include propylene glycol, polyethylene glycol, dimethylsulphoxide, decylmethylsulphoxide, azones, N-methylpyrrolidone, diethyltoluamide, ethanol, isopropyl myristate, isopropyl palmitate, oleic acid and its esters, medium-chain triglycerides, dimethyl isosorbitol, 2-octyldodecanol, branched fatty acids, benzyl alcohol, urea, salicylates and surfactants.

Viscosity enhancers or thickeners can be included. One benefit of including such enhancers is to prevent the formulation from spreading beyond the site of application. In one embodiment, Balsam Fir is a pharmaceutically acceptable viscosity enhancer. Another benefit of increasing the viscosity of the formulation is provided below in the section discussing thixotropic agents. Thickeners include suitable polymers such as carbomer, hydroxypropyl methylcellulose, hydroxyethylcellulose, PVM/MA decadiene cross-polymer and acrylates. Two or more thickeners can be added.

Spreading oils can also be included. One benefit for including such oils is for better distribution on surfaces, in particular on the skin. Spreading oils are understood as those oily liquids which are distributed particularly easily on the skin. They are known as such in cosmetics. The following compounds are suitable spreading agents: silicone oil, fatty acid esters, such as ethyl stearate, di-n-butyl adipate, hexyl laurate and dipropylene glycol pelargonate, esters of a branched fatty acid of medium chain length with saturated $C_{16}$-$C_{18}$ fatty alcohols, isopropyl myristate, isopropyl palmitate, caprylic/capric acid esters of saturated fatty alcohols of $C_{12}$-$C_{18}$ chain length, isopropyl stearate, oleyl oleate, decyl oleate, ethyl oleate, ethyl lactate, waxy fatty acid esters, such as synthetic duck uropygial gland fat, dibutyl phthalate, diisopropyl adipate, ester mixtures related to the latter and the like. Other elements that can be included are emollients, such diisopropyl adipate/isohexadecane dimethicone, occlusive agents, such as example cyclomethicone, trimethylsiloxysilicate, glycereth-26 or polyquaternium-7, emulsifiers, such as cetyl alcohol, stearyl, stearic acid, glyceryl stearate, propylene glycol isostearoyl-sodium isostearoyl, a lactylate, polyoxyethylene (100) stearate, skin conditioners, moisturizers, humectants, such as propylene glycol or glycerin, preservatives, such as phenoxyethanol and parabens, pH adjusting agents, surfactants, chelating agents, such as disodium EDTA or sodium citrate, tackifying agents, fragrances and other compounds.

Other compounds that can be included in the topical formulation include antimicrobial or antibacterial compositions, including, but not limited to, benzyl alcohol. The compositions of this invention may be used in conjunction with other active ingredients and in conjunction with other treatment regimens.

Encapsulation

The phase II enzyme inducer precursors and activating agents can be encapsulated in a carrier. Suitable carriers are described in U.S. Pat. No. 7,205,003, hereby incorporated in its entirety for all purposes. Below are non-limiting means by which the encapsulation can be obtained.

Micelles

Micelles provided herein can comprise surfactant molecules arranged such that their polar headgroups form an outer spherical shell, while their hydrophobic, hydrocarbon chains are oriented towards the center of the sphere, forming a core. The precursor and agent are encapsulated within the core of the micelle. Surfactants suitable for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl-8 dodecyl ether, polyoxyl-12 dodecyl ether, nonoxynol 10, and nonoxynol 30.

Liposomes

Liposomes provided herein are microscopic vesicles having a lipid wall comprising a lipid bilayer. Liposomal preparations herein include cationic (positively charged), anionic (negatively charged), and neutral preparations. Cationic liposomes include N[1-2,3-dioleyloxy)propyl]-N,N,N-triethylammonium (DOTMA). Anionic and neutral liposomes can be easily prepared using materials such as phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE). These materials can also be mixed with DOTMA in appropriate ratios.

Microspheres

Microspheres provided herein can comprise micro- or nano-scale carriers that are made of polymers, both synthetic and natural. Additional nomenclature describing microspheres include, but are not limited to, spheres, beads, particles, carriers, microbeads, microparticles, microcarriers, nanospheres, nanobeads, nanoparticles, and nanocarriers.

Polymeric materials suitable for the microspheres provided herein include those that are described in U.S. Pat. No. 6,423,345, hereby incorporated by reference in its entirety for all purposes, including poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene tereptalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivatized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate) (jointly referred to herein as "polyacrylic acids"), poly (butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art. Natural polymers including agarose and alginate are also suitable for the microspheres.

Any of the above carriers can include proteins, lectins, and other biological materials. As an example, the microspheres can be Concanavalin A-sepharose gels (Con-A gels). When immobilized on Con-A gels, myrosinase was found to retain its enzymatic activity and can remain stable indefinitely without refrigeration, as supported by Example 1.

The precursors and activating agents can be encapsulated into the carriers using known techniques in the art, including microspheres described in U.S. Pat. No. 6,423,345, already incorporated by reference above, including solvent evaporation, hot melt microencapsulation, solvent removal, and spray drying of microspheres.

In one embodiment, the microsphere is comprised of a block copolymer.

In another embodiment, the microsphere is a hydrogel.

Tablets

In other embodiments, the formulation includes tablets or pills which are formulated to separate the phase II enzyme inducer and the activating agent. Incorporation of the phase II enzyme into one tablet and the activating agent into a second tablet is also envisioned. The components of these tablets can interact in the mouth upon chewing of the pills at the same time or in the digestive track during digestion. Similarly, Applicants also envision the use of a single pill to incorporate both the phase II enzyme inducer and the activating agent. These components can be included in separate parts of the tablet such as a core and outer portion or two halves of the tablet. In both of these instances, the phase II enzyme inducer and activating agent would remain separate until chewing or mixing in the digestive track of the individual taking the tablet.

Beverages

In other embodiments, the formulation includes liquids and beverages. These beverages are formulated to include the presence of liposomes inside the beverage so that either the phase II enzyme or the activating agent is contained in the liposome and the other component is present in the rest of the beverage. Once the liquid is ingested, it is formulated to allow for the mixing of the liposomes with the rest of the beverage and interaction of the phase II enzyme and activating agent.

Nutritional Bars

In other embodiments, the formulation includes nutritional bars with separate portions for the phase II enzyme and activation agent. The activating agent could be present, for example, in seeds placed on the outside of the bar, and the phase II enzyme incorporated into the remainder of the nutritional bar. Upon ingestion, both portions of the bar would mix, leading to contact between the two components.

Separating Phase II Enzyme Inducer Precursors and Their Activating Agents

The precursors and activating agents provided herein can be separated such that their contact with each other is substantially reduced. By reducing contact, the activating agents do not prematurely activate the precursors, thereby allowing the topical formulation to remain viable in storage. Below are non-limiting means by which the separation can be performed.

By Encapsulation

Encapsulation has been described above. By encapsulating the precursors and activating agents, they are contained such that there is substantially reduced contact with each other. The precursors and activating agents can be separately encapsulated or encapsulated within the same carrier.

For separate encapsulations, the precursors and activating agents can be encapsulated in the same or different type of carrier. After encapsulation, the carriers can be mixed in a medium selected from the different topical formulation mediums described above.

For encapsulation within the same carrier, the precursors and activating agents are separated by a layer of material. The material can be the same or different from the material that makes up the carrier. In one embodiment, the carrier is double-layered, with the precursor in one layer and the activating agent in another layer.

In one embodiment, the carrier is non-porous.

In another embodiment, the carrier can withstand the pressure or shear forces exerted upon it when the medium is forced out of a compartment, but can break apart due to pressure or shear forces acting upon it during application (i.e. rubbing) on the skin surface.

In another embodiment, only one of the precursor and activating agent is encapsulated.

In another embodiment, both the precursor and activating agent are encapsulated.

By Device

Devices that can contain topical formulations are provided to reduce the contact between phase II enzyme inducer precursors and their activating agents. The devices can include separate chambers that each contain either phase II enzyme inducer precursor or the activating agent.

Devices that fall within this category include, but are not limited to, a syringe, tube, and dispensing apparatus. Devices with various design features that provide a dual- or multi-component system fall within the scope of the devices provided. Dispensing apparatuses applicable to the topical formulations provided are described in U.S. Pat. Nos. 7,213,994 and 7,192,179, both of which are incorporated by reference in their entirety for all purposes.

In one embodiment, the device includes different topical formulation mediums for each of the phase II enzyme inducer precursor and activating agent.

In another embodiment, the device includes a heating element to heat the topical formulation such that the medium is less viscous and flows more freely.

By Topical Formulation Medium

Thixotropic materials have a high viscosity under static conditions, but act as liquids under shear stress. Examples of commonly used thixotropic materials are toothpaste and ketchup. Materials with similar properties are applicable in separating the phase II enzyme inducer precursor and activating agent.

Because of the highly viscous nature of thixotropic materials, compounds provided within the materials do not contact each other under static conditions. Thus, a topical formulation having a thixotropic medium provides for a formulation that effectively separates phase II enzyme inducer precursor and its activating agent. Pharmaceutical and cosmetic formulations in a thixotropic material are described in U.S. Pat. Nos. 6,967,023 and 6,994,863, which are incorporated by reference in their entirety for all purposes.

In one embodiment, separated precursor and activating agents are not encapsulated.

In another embodiment, separate precursor and activating agents are encapsulated, either in separate carriers or together in one carrier.

In another embodiment, the thixotropic material is provided in a device.

Bringing the Phase II Enzyme Inducer Precursor and Activating Agent into Contact The phase II enzyme inducer precursors and their activating agents can be brought together by a variety of means. Such means can depend upon the manner in which the precursors and activating agents are placed in the topical formulation. Non-limiting means of bringing together the two compounds are described below.

By Force

The precursor and activating agent can be made to come into contact through a physical force acted on the topical formulation.

For the encapsulation method described above, rubbing the topical formulation onto the skin surface breaks apart the carrier, i.e. microspheres, micelles, or liposomes, thereby releasing the phase II enzyme inducer and/or activating agent. As described above, the carrier should have physical properties that can withstand pressure or shear forces exerted upon it when the medium is forced out of a compartment, but be able to break apart due to pressure or shear forces acting upon it during application (i.e. rubbing) on the skin surface.

For topical formulations with precursor and activating agents separated by containers and for topical formulations with a thixotropic medium where the precursor and activating agent are not encapsulated, the force is simply what is necessary to dispense the medium from its container or containers.

In one embodiment, the force is pressure.

In another embodiment, the force is shear stress.

By Environmental Conditions

The precursor and activating agent can be made to come into contact through changes in their environment, including, but not limited to, changes in pH, moisture, and temperature.

In one embodiment, room temperature will activate conversion of the precursor agent by the activating agent into phase II enzyme inducers.

In another embodiment, body temperature will activate conversion of the precursor agent by the activating agent into phase II enzyme inducers.

Treatment and Prevention

Once the phase II enzyme inducer precursor and activating agent combine to produce the phase II enzyme inducer, the inducer is capable of both repairing damage caused by skin ailments or preventing damage that has not yet been initiated. Thus, the topical formulation can be applied either after sun exposure for treatment purposes, or before sun exposure as a preventative measure.

EXAMPLE 1

Long-Term Stability of Myrosinase on Concanavalin A-Sepharose Gels

Con-A gel (1 ml) was packed in a 3 ml syringe, washed with 5 portions of 5 ml of 10 mM midazole, 1 mD EDTA, 1 mM DTT, 30% glycerol, pH 6.0. Subsequently, 10 ml of purified myrosinase (2.9 units/ml) (from 7 day-old daikon sprouts as described in Shikita et al. *Biochem J.* (1999) 341: 725-732) were applied to the column and the effluent collected and reapplied to the column 3 more times until no activity was detected in the effluent. After washing 5 times with 5 ml of 33 mM potassium phosphate buffer (pH 6.0), 1 mM EDTA, and 0.5 mM ascorbate, the gel was transferred to a 10 ml syringe and mixed with 10 ml of 10 mM sinigrin in 33 mM potassium phosphate buffer. Aliquots (20 µl of the solution was withdrawn from the mixture every 30 sec., diluted with 0.98 ml of the 33 mM phosphate buffer, and the absorbance was measured at 227 nm against the same buffer. After 10 collections (5 min), the gel was washed with 3 portions of 5 ml of 33 mM potassium phosphate buffer, and 3 portions of 5 ml 10 mM midazole, 1 mM EDTA, 1 mD DTT, 30% glycerol, pH 6.0, and stored at 4° C. for the next test.

Immobilized enzyme showed high activity, with more than 25 µmol of sinigrin hydrolyzed. There were no significant changes of activity over at least the next 7 days when it was kept at 4° C. in 20% glycerol. Other experiments showed that there was no significant elution of the enzyme from the column under conditions required for hydrolysis and that the immobilized enzyme was stable even at room temperature for a period of several weeks.

What is claimed is:

1. A dispensing apparatus comprising a formulation comprising:
   (a) at least one phase II enzyme inducer precursor and
   (b) at least one activating agent,
   wherein contact between said precursor and agent is substantially reduced during storage and the formulation is a topical formulation;
   wherein the precursor and the agent are each separately encapsulated in a carrier; and wherein the carrier is a micelle, a liposome, or a microsphere.

2. The dispensing apparatus of claim 1, wherein said precursor is a glucosinolate.

3. The dispensing apparatus of claim 2, wherein said glucosinolate is glucoraphanin.

4. The dispensing apparatus of claim 1, wherein said agent is a myrosinase.

5. The dispensing apparatus of claim 1, wherein said inducer is an isothiocyanate.

6. The dispensing apparatus of claim 5, wherein said isothiocyanate is sulforaphane.

7. The dispensing apparatus of claim 1, wherein said precursor and agent are placed in a thixotropic medium.

8. The dispensing apparatus of claim 1, wherein the formulation is selected from the group consisting of a cream, a lotion, a gel, an ointment, a paste, and an aerosol spray.

9. The dispensing apparatus of claim 1, wherein the formulation is sterile at least prior to a first use of the formulation.

10. The dispensing apparatus of claim 1, further comprising an antimicrobial composition.

11. The dispensing apparatus of claim 10, wherein the antimicrobial composition comprises benzyl alcohol.

12. A method of making a formulation comprising:
   (a) providing at least one phase II enzyme inducer precursor;
   (b) providing at least one activating agent;
   (c) providing a medium; and
   (d) forming the formulation by including elements (a), (b), and (c) therein,
   wherein the formulation is selected from the group consisting of a topical formulation, a pill, a beverage, and a food;
   wherein the precursor and the agent are each separately encapsulated in a carrier; and wherein the carrier is a micelle, a liposome, or a microsphere.

13. The method of claim 12, wherein said precursor is a glucosinolate.

14. The method of claim 12, wherein said activating agent is a myrosinase.

15. The method of claim 12, wherein the topical formulation is a cream, a lotion, a gel, an ointment, a paste, or an aerosol.

16. The method of claim 12, further providing an antimicrobial composition.

17. The method of claim 12, wherein the medium is a thixotropic material.

18. A method of treating skin ailments comprising:
   (a) providing a topical formulation; and
   (b) applying the formulation to the surface of skin with the dispensing apparatus of claim 1.

19. The method of claim 12, wherein the topical formulation comprises at least one phase II enzyme inducer precursor and at least one activating agent such that contact between said precursor and said agent is substantially reduced.

20. The method of claim 19, wherein said precursor and said agent are each encapsulated in a carrier selected from the group comprising a micelle, a liposome, and a microsphere.

21. The method of claim 20, wherein the topical formulation is a cream, a lotion, a gel, an ointment, a paste, or an aerosol spray.

22. A method of treating skin ailments comprising:
   (a) providing a topical formulation in a container, wherein the topical formulation comprises at least one phase II enzyme inducer precursor and at least one activating agent, wherein contact between the precursor and agent is substantially reduced;
   (b) mixing the precursor and agent together to create a mixture; and
   (c) applying the mixture to the surface of skin.

23. The method of claim 22, wherein the container is selected from the group comprising a syringe, a tube, and a dispensing apparatus.

24. The method of claim 22, further comprising a medium selected from the group comprising a cream, a lotion, a gel, an ointment, and a paste.

25. The method of claim 22, wherein said precursor and said agent are encapsulated in a carrier selected from the group comprising a micelle, a liposome, and a microsphere.

26. The method of claim 25, wherein step (b) comprises providing pressure or stress onto said medium such that said carrier is not broken or does not release said precursor or activating agent.

27. A method of treating skin cancer comprising:
(a) providing a topical formulation comprising at least one phase II enzyme inducer precursor and at least one activating agent, wherein the precursor and agent are each encapsulated in a carrier such that contact between said precursor and said agent is substantially reduced;
(b) mixing the carriers containing said precursor and said agent together to create a mixture; and
(c) applying the mixture to the surface of skin.

28. The method of claim 27, wherein said precursor is a glucosinolate.

29. The method of claim 27, wherein said agent is a myrosinase.

30. The method of claim 27, wherein said phase II enzyme is an isothiocyanate.

31. The method of claim 27, wherein said topical formulation further comprises a dermal penetration-enhancing compound.

32. The method of claim 27, wherein the method of treating comprises applying the mixture to the surface of skin after skin damage.

33. The method of claim 27, wherein the method of treating comprises applying the mixture to the surface of skin before skin damage.

* * * * *